(12) United States Patent
Park et al.

(10) Patent No.: US 10,390,781 B2
(45) Date of Patent: Aug. 27, 2019

(54) X-RAY APPARATUS AND METHOD OF CONTROLLING X-RAY APPARATUS

(71) Applicant: SAMSUNG ELECTRONICS CO., LTD., Suwon-si (KR)

(72) Inventors: Min-cheol Park, Bucheon-si (KR); Phill-gu Jung, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 165 days.

(21) Appl. No.: 15/505,761

(22) PCT Filed: Aug. 10, 2015

(86) PCT No.: PCT/KR2015/008338
§ 371 (c)(1),
(2) Date: Feb. 22, 2017

(87) PCT Pub. No.: WO2016/028020
PCT Pub. Date: Feb. 25, 2016

(65) Prior Publication Data
US 2017/0281107 A1 Oct. 5, 2017

(30) Foreign Application Priority Data

Aug. 22, 2014 (KR) .................. 10-2014-0109961

(51) Int. Cl.
*A61B 6/00* (2006.01)
*A61B 6/04* (2006.01)

(52) U.S. Cl.
CPC .......... *A61B 6/502* (2013.01); *A61B 6/0414* (2013.01); *A61B 6/4464* (2013.01); *A61B 6/465* (2013.01); *A61B 6/488* (2013.01); *A61B 6/542* (2013.01)

(58) Field of Classification Search
CPC ..................................................... A61B 6/542
See application file for complete search history.

(56) References Cited

U.S. PATENT DOCUMENTS 6,151,383 A * 11/2000 Xue .................. A61B 6/00
378/108
6,795,526 B2 9/2004 Kump et al.
(Continued)

FOREIGN PATENT DOCUMENTS

JP 7-77749 A 3/1995
JP 2003-284708 A 10/2003
(Continued)

OTHER PUBLICATIONS

International Search Report & Written Opinion dated Nov. 27, 2015 issued by the International Searching Authority in counterpart International Application No. PCT/KR2015/008338 (PCT/ISA/220/210/237).

(Continued)

*Primary Examiner* — Dani Fox
(74) *Attorney, Agent, or Firm* — Sughrue Mion, PLLC

(57) ABSTRACT

Provided is an X-ray apparatus. The X-ray apparatus includes: an X-ray photographing unit configured to acquire first image information by irradiating an X-ray of a first dose to an object; a control unit configured to determine existence/nonexistence of a density abnormality of the object on the basis of the first image information; and an output unit configured to display information about the existence/nonexistence of the density abnormality.

13 Claims, 16 Drawing Sheets

(56) References Cited

U.S. PATENT DOCUMENTS

| | | |
|---|---|---|
| 7,209,543 B2 | 4/2007 | Strommer |
| 2003/0216631 A1 | 11/2003 | Bloch et al. |
| 2009/0097730 A1 | 4/2009 | Kasai et al. |
| 2010/0145197 A1 | 6/2010 | Stapf et al. |
| 2012/0035462 A1 | 2/2012 | Maurer, Jr. et al. |
| 2014/0079185 A1 | 3/2014 | Omi et al. |

FOREIGN PATENT DOCUMENTS

| | | |
|---|---|---|
| JP | 2006-204744 A | 8/2006 |
| WO | 2006/116700 A2 | 11/2006 |
| WO | 2012102052 A1 | 8/2012 |
| WO | 2013027816 A1 | 2/2013 |

OTHER PUBLICATIONS

Communication dated Nov. 30, 2016 issued by the European Patent Office in counterpart European Patent Application No. 16175022.9.
Communication issued May 15, 2018, issued by the European Patent Office in counterpart European Patent Application No. 15834492.9.

\* cited by examiner

X-RAY APPARATUS AND METHOD OF CONTROLLING X-RAY APPARATUS

TECHNICAL FIELD

One or more exemplary embodiments relate to X-ray apparatuses and methods of controlling the X-ray apparatuses, and more particularly, to X-ray apparatuses capable of displaying information about the existence/nonexistence of a density abnormality and methods of controlling the X-ray apparatuses.

BACKGROUND ART

In general, X-rays are electromagnetic waves having a wavelength of about 0.01 Å to about 100 Å. Since the X-rays have a property that allows them to penetrate objects, they may be widely used in medical equipment, which photograph the insides of organisms, or nondestructive testing equipment for general industry.

An X-ray apparatus may acquire an X-ray image of an object by transmitting X-rays, which are emitted from an X-ray source, through the object and detecting the intensity differences between the transmitted X-rays by an X-ray detector. The X-ray apparatus may detect an internal structure of the object from the X-ray image to diagnose the object. The X-ray apparatus may easily detect the internal structure of the object on the basis of the principle that the X-ray transmittance varies according to the densities of the object and the atomic numbers of atoms constituting the object. As the X-ray wavelength decreases, the X-ray transmittance and the screen brightness thereof increase.

Mammography uses an X-ray apparatus to capture an X-ray image of a breast. Mammography is one of the best non-invasive testing methods for detecting breast cancer. In the related art, since a user has difficulty in detecting an error, which may be caused by a filter error, a collimation error, or an error due to an implant inserted into a breast, from a pre-shot image, the user has to perform rephotographing after acquisition of a main-shot image.

DISCLOSURE

Technical Solution

One or more exemplary embodiments include X-ray apparatuses and systems that may easily determine whether to perform re-photographing.

Additional aspects will be set forth in part in the description which follows and, in part, will be apparent from the description, or may be learned by practice of the presented exemplary embodiments.

According to one or more exemplary embodiments, an X-ray apparatus includes: an X-ray photographing unit configured to acquire first image information by irradiating an X-ray of a first dose to an object; a control unit configured to determine existence/nonexistence of a density abnormality of the object on the basis of the first image information; and an output unit configured to display information about the existence/nonexistence of the density abnormality.

The control unit may acquire a density of the object from the first image information and compares the acquired density with a predetermined reference value to determine the existence/nonexistence of the density abnormality.

The X-ray apparatus may further include input unit configured to receive an input about rephotographing of the first image information from a user.

When the rephotographing is not requested in the input, the X-ray photographing unit may further acquire second image information by irradiating an X-ray of a second dose greater than the first dose.

The output unit may further display a degree of the density abnormality based on a density of the object.

The output unit may further display a type of the density abnormality based on a density of the object.

The control unit may acquire a density of the object on the basis of pixel values of an effective auto exposure control (AEC) field corresponding to a predetermined region of the object in the first image information to determine the existence/nonexistence of the density abnormality.

When the acquired density is a value between a lower-limit threshold value and an upper-limit threshold value, the control unit determines that the density abnormality does not exist.

When the density abnormality exists, the output unit may output an alarm about the density abnormality.

The output unit may further display a message about the existence/nonexistence of the density abnormality and a first image based on the first image information.

The X-ray photographing unit may determine an irradiation dose of the X-ray of the second dose on the basis of a density of the object and irradiates the X-ray of the second dose according to the determined irradiation dose to acquire the second image information.

The object may comprise a breast.

The density of the object may be acquired on the basis of the lowest pixel value among the pixel values of the effective AEC field.

When the rephotographing is requested in the input, the X-ray photographing unit may modify the first image information by rephotographing the object.

The X-ray apparatus may further include a compression paddle configured to compress the object.

According to one or more exemplary embodiments, a method of controlling an X-ray apparatus includes: acquiring first image information by irradiating an X-ray of a first dose to an object; determining existence/nonexistence of a density abnormality of the object on the basis of the first image information; and displaying information about the existence/nonexistence of the density abnormality.

The determining of the existence/nonexistence of the density abnormality may include acquiring a density of the object from the first image information and comparing the acquired density with a predetermined reference value to determine the existence/nonexistence of the density abnormality.

The method may further include: receiving an input about rephotographing of the first image information from a user; and acquiring second image information by irradiating an X-ray of a second dose greater than the first dose, when the rephotographing is not requested in the input.

The method may further include displaying a degree of the density abnormality on the basis of a density of the object.

The method may further include displaying a type of the density abnormality on the basis of a density of the object.

A density of the object may be acquired on the basis of pixel values of an effective auto exposure control (AEC) field corresponding to a predetermined region of the object in the first image information.

The determining of the existence/nonexistence of the density abnormality may include determining that the density abnormality does not exist, when the acquired density is a value between a lower-limit threshold value and an upper-limit threshold value.

The displaying of the information about the existence/nonexistence of the density abnormality may include outputting an alarm about the density abnormality and displaying a first image based on the first image information.

The displaying of the information about the existence/nonexistence of the density abnormality comprises displaying a message about the existence/nonexistence of the density abnormality and a first image based on the first image information.

The acquiring of the second image information may include: determining an irradiation dose of the X-ray of the second dose on the basis of a density of the object and a thickness of the object; and irradiating the X-ray of the second dose according to the determined irradiation dose to acquire the second image information. The object comprises a breast.

The density of the object may be acquired on the basis of the lowest pixel value among the pixel values of the effective AEC field.

The method may further include modifying the first image information by rephotographing the object, when the rephotographing is requested in the input.

The method may further include compressing the object.

According to one or more exemplary embodiments, a non-transitory computer-readable recording medium stores a program that performs the method of any one of above when executed by a computer.

According to one or more exemplary embodiments, an X-ray apparatus includes: an X-ray irradiating unit configured to irradiate an X-ray of a first dose to an object; a detection unit configured to acquire first image information by detecting an X-ray that has penetrated the object; a control unit configured to determine existence/nonexistence of a density abnormality of the object on the basis of the first image information; and an output unit configured to display information about the existence/nonexistence of the density abnormality.

According to one or more exemplary embodiments, a workstation configured to control an X-ray apparatus, the workstation includes: a control unit configured to receive first image information, which is acquired by irradiating an X-ray of a first dose to an object, from the X-ray apparatus and determine existence/nonexistence of a density abnormality of the object on the basis of the first image information; and an output unit configured to display information about the existence/nonexistence of the density abnormality.

According to one or more exemplary embodiments, an X-ray system comprising an X-ray apparatus and a workstation configured to control the X-ray apparatus, the X-ray system includes: an X-ray apparatus comprising an X-ray photographing unit configured to acquire first image information by irradiating an X-ray of a first dose to an object and a control unit configured to control the X-ray photographing unit; and a workstation comprising a control unit configured to receive first image information, which is acquired by irradiating the X-ray of the first dose to an object, from the X-ray apparatus and determine existence/nonexistence of a density abnormality of the object on the basis of the first image information and an output unit configured to display information about the existence/nonexistence of the density abnormality.

DESCRIPTION OF DRAWINGS

These and/or other aspects will become apparent and more readily appreciated from the following description of exemplary embodiments, taken in conjunction with the accompanying drawings in which.

MODE FOR INVENTION

Figure 1:
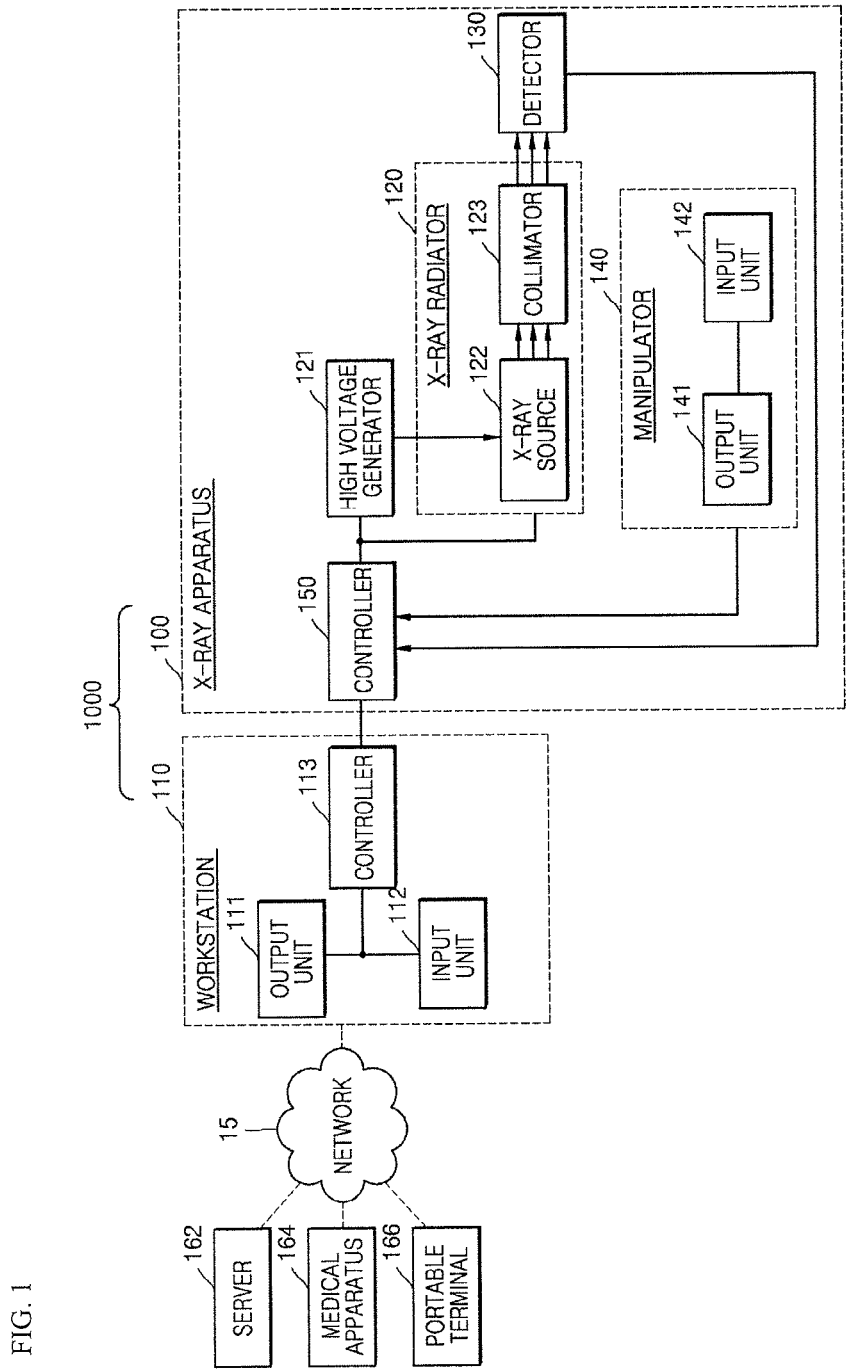
FIG. 1 is a block diagram of an X-ray system.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The attached drawings for illustrating exemplary embodiments of the inventive concept are referred to in order to gain a sufficient understanding of the inventive concept, the merits thereof, and the objectives accomplished by the implementation of the inventive concept. The inventive concept may, however, be embodied in many different forms and should not be construed as being limited to the exemplary embodiments set forth herein; rather, these exemplary embodiments are provided such that this disclosure will be thorough and complete, and will fully convey the inventive concept to those of ordinary skill in the art.

The terms used in the present specification will be briefly described, and then the inventive concept will be described in detail.

The terms used in the present specification are those general terms currently widely used in the art in consideration of functions in regard to the exemplary embodiments, but the terms may vary according to the intentions of those of ordinary skill in the art, precedents, or new technology in the art. Also, specified terms may be selected by the applicant, and in this case, the detailed meanings thereof will be described in the detailed description of the exemplary embodiments. Thus, the terms used in the present specification should be understood not as simple names but based on the meaning of the terms and the overall description of the exemplary embodiments.

In the present specification, an "image" may mean multi-dimensional data formed of discrete image elements (e.g., pixels in a two-dimensional (2D) image and voxels in a three-dimensional (3D) image). Examples of the image may include medical images of objects that are acquired by X-ray apparatuses, computed tomography (CT) apparatuses, magnetic resonance imaging (MRI) apparatuses, ultrasound apparatuses, or any other medical imaging apparatuses.

Also, an "object" may be a human, an animal, or a part of a human or animal. For example, the object may include an organ, such as a liver, a heart, a womb, a brain, a breast, or an abdomen, a blood vessel, or any combination thereof. Also, the object may be a phantom. The phantom may be a material having a volume, a density, and an effective atomic number that are approximately the same as those of an organism. For example, the phantom may include a spherical phantom having similar properties to a human body.

Also, a "user" may be, but is not limited to, a medical expert, such as a medical doctor, a nurse, a medical laboratory technologist, or a medical imaging expert, or a technician who repairs medical apparatuses.

An X-ray apparatus is a medical imaging apparatus that acquires images of internal structures of a human body by transmitting X-rays through the human body. The X-ray apparatus may acquire medical images of objects more simply within a shorter time than other medical imaging apparatuses including an MRI apparatus and a CT apparatus. Therefore, the X-ray apparatus is widely used in simple chest photographing, simple abdomen photographing, skeleton photographing, nasal sinus photographing, neck soft tissue photographing, and breast photographing.

FIG. 1 is a block diagram of an X-ray system 1000.

Referring to FIG. 1, the X-ray system 1000 includes an X-ray apparatus 100 and a workstation 110. The X-ray apparatus 100 illustrated in FIG. 1 may be a fixed-type X-ray apparatus or a mobile X-ray apparatus. The X-ray apparatus 100 may include an X-ray irradiating unit 120, a high voltage generating unit 121, a detection unit 130, an operation unit 140, and a control unit 150. The control unit 150 may control overall operations of the X-ray apparatus 100.

The high voltage generating unit 121 generates a high voltage for generating X-rays, and applies the high voltage to an X-ray source 122.

The X-ray irradiating unit 120 includes the X-ray source 122 that receives the high voltage from the high voltage generating unit 121 to generate and irradiate X-rays, and a collimator 123 for guiding a path of the X-ray irradiated from the X-ray source 122 and adjusting an irradiation region irradiated by the X-ray.

The X-ray source 122 includes an X-ray tube that may be realized as a vacuum tube diode including a cathode and an anode. An inside of the X-ray tube is set to be in a high vacuum state of about 10 mmHg, and a filament of the anode is heated to a high temperature to generate thermal electrons. The filament may be a tungsten filament, and a voltage of about 10 V and a current of about 3 to 5 A may be applied to an electric line connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is irradiated outside through a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generating unit 121 and a magnitude of the tube voltage may be expressed by a peak value (kVp). When the tube voltage increases, a velocity of the thermal electrons increases, and accordingly, an energy of the X-ray (photon energy) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detection unit 130 detects an X-ray that is irradiated from the X-ray irradiating unit 120 and has been transmitted through an object. The detection unit 130 may be a digital detection unit. The detection unit 130 may be implemented by using a thin film transistor (TFT) or a charge coupled device (CCD). Although the detection unit 130 is included in the X-ray apparatus 100 in FIG. 1, the detection unit 130 may be an X-ray detector that is a separate device capable of being connected to or separated from the X-ray apparatus 100.

The X-ray apparatus 100 may further include an operation unit 140 for providing a user with an interface for operating the X-ray apparatus 100. The operation unit 140 may include an output unit 141 and an input unit 142. The input unit 142 may receive from a user a command for operating the X-ray apparatus 100 and various types of information related to X-ray photographing. The control unit 150 may control or operate the X-ray apparatus 100 according to the information received by the input unit 142. The output unit 141 may output sound representing information related to a photographing operation such as the X-ray irradiation under the control of the control unit 150.

The workstation 110 and the X-ray apparatus 100 may be connected to each other by wire or wirelessly. When they are connected to each other wirelessly, a device (not illustrated) for synchronizing clock signals with each other may be further included. The workstation 110 and the X-ray apparatus 100 may exist within physically separate spaces.

The workstation 110 may include an output unit 111, an input unit 112, and a control unit 113. The output unit 111 and the input unit 112 provide a user with an interface for operating the workstation 110 and the X-ray apparatus 200. The control unit 113 may control the workstation 110 and the X-ray apparatus 200.

The X-ray apparatus 100 may be controlled through the workstation 110 or may be controlled by the control unit 150 included in the X-ray apparatus 100. Accordingly, a user may control the X-ray apparatus 100 through the workstation 110 or may control the X-ray apparatus 100 through the operation unit 140 and the control unit 150 included in the X-ray apparatus 100. In other words, a user may remotely control the X-ray apparatus 100 through the workstation 110 or may directly control the X-ray apparatus 100.

Although the control unit 113 of the workstation 110 is separate from the control unit 150 of the X-ray apparatus 100 in FIG. 1, FIG. 1 is only an example. As another example, the control units 113 and 150 may be integrated into a single control unit, and the single control unit may be included in only one of the workstation 110 and the X-ray apparatus 100. Hereinafter, the control units 113 and 150 may denote the control unit 113 of the workstation 110 and/or the control unit 150 of the X-ray apparatus 100.

The output unit 111 and the input unit 112 of the workstation 110 may provide a user with an interface for operating the X-ray apparatus 100, and the output unit 141 and the input unit 142 of the X-ray apparatus 100 may also provide a user with an interface for operating the X-ray apparatus 100. Although the workstation 110 and the X-ray apparatus 100 include the output units 111 and 141, respectively, and the input units 112 and 142, respectively, in FIG. 1, exemplary embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touchscreen, a voice recognizer, a fingerprint recognizer, an iris recognizer, and other input devices which are well known to those of ordinary skill in the art. The user may input, through the input units 112 and 142, a command for irradiating the X-ray, and the input units 112 and 142 may include a switch for inputting the command. The switch may be configured so that an irradiation command for irradiating the X-ray may be input only when the switch is pushed in two steps.

In other words, when the user pushes the switch, a prepare command for performing a pre-heating operation for X-ray irradiation may be input, and in this state, when the user pushes the switch further, an irradiation command for performing substantial X-ray irradiation may be input. When the user operates the switch as described above, the control units 113 and 150 generate signals corresponding to the commands input through the switch operation, that is, a prepare signal, and transmit the generated signals to the high voltage generating unit 121 that generates a high voltage for generating the X-ray.

When the high voltage generating unit 121 receives the prepare signal from the control units 113 and 150, the high voltage generating unit 121 starts a pre-heating operation, and when the pre-heating is completed, the high voltage generating unit 121 outputs a ready signal to the control units 113 and 150. In addition, the detection unit 130 also needs to prepare to detect the X-ray, and thus the high voltage generating unit 121 performs the pre-heating operation and the control units 113 and 150 transmit a prepare signal to the detection unit 130 so that the detection unit 130 may prepare to detect the X-ray transmitted through the object. The detection unit 130 prepares to detect the X-ray in response to the prepare signal, and when the preparing for the detection is completed, the detection unit 130 outputs a ready signal to the control units 113 and 150.

When the pre-heating operation of the high voltage generating unit 121 is completed and the detection unit 130 is ready to detect the X-ray, the control units 113 and 150 transmit an irradiation signal to the high voltage generating unit 121, the high voltage generating unit 121 generates and applies the high voltage to the X-ray source 122, and the X-ray source 122 irradiates the X-ray.

When the control units 113 and 150 transmit the irradiation signal to the high voltage generating unit 121, the control units 113 and 150 may transmit a sound output signal to the output units 111 and 141 so that the output units 111 and 141 output a predetermined sound and the object may recognize the irradiation of the X-ray. The output units 111 and 141 may also output a sound representing information related to photographing in addition to the X-ray irradiation. In FIG. 1, the output unit 141 is included in the operation unit 140; however, exemplary embodiments are not limited thereto, and the output unit 141 or a portion of the output unit 141 may be located elsewhere. For example, the output unit 141 may be located on a wall of an examination room in which the X-ray photographing of the object is performed.

The control units 113 and 150 control locations of the X-ray irradiating unit 120 and the detection unit 130, photographing timing, and photographing conditions, according to photographing conditions set by the user.

In more detail, the control units 113 and 150 control the high voltage generating unit 121 and the detection unit 130 according to the command input through the input units 112 and 142 so as to control irradiation timing of the X-ray, an intensity of the X-ray, and a region irradiated by the X-ray. In addition, the control units 113 and 150 adjust the location of the detection unit 130 according to a predetermined photographing condition, and controls operation timing of the detection unit 130.

Furthermore, the control units 113 and 150 generate a medical image of the object by using image data received through the detection unit 130. In detail, the control units 113 and 150 may receive the image data from the detection unit 130, and then, generate the medical image of the object by removing noise from the image data and adjusting a dynamic range and interleaving of the image data.

The output units 111 and 141 may output the medical image generated by the control units 113 and 150. The output units 111 and 141 may output information that is necessary for the user to operate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to those of ordinary skill in the art.

The workstation 110 illustrated in FIG. 1 may further include a communication unit (not illustrated) that may be connected to a server 162, a medical apparatus 164, and a portable terminal 166 through a network 160.

The communication unit may be connected to the network 160 by wire or wirelessly to communicate with the server 162, the medical apparatus 164, or the portable terminal 166. The communication unit may transmit or receive data related to diagnosis of the object through the network 160, and may also transmit or receive medical images captured by the medical apparatus 164, for example, a CT apparatus, an MRI apparatus, or an X-ray apparatus. Moreover, the communication unit may receive a medical history or treatment schedule of an object (e.g., a patient) from the server 162 to diagnose a disease of the object. Also, the communication unit may perform data communication with the portable terminal 166 such as a mobile phone, a personal digital assistant (PDA), or a laptop computer of a medical doctor or a client, as well as the server 162 or the medical apparatus 164 in a hospital.

The communication unit may include one or more elements enabling communication with external apparatuses. For example, the communication unit may include a short-range communication module, a wired communication module, and a wireless communication module.

The short-range communication module refers to a module for performing short-range communication with an apparatus located within a predetermined distance. Examples of short-range communication technology may include, but are not limited to, a wireless local area network (LAN), Wi-Fi, Bluetooth, ZigBee, Wi-Fi Direct (WFD), ultra wideband (UWB), infrared data association (IrDA), Bluetooth low energy (BLE), and near field communication (NFC).

The wired communication module refers to a module for communicating by using an electric signal or an optical signal. Examples of wired communication technology may include wired communication techniques using a twisted-pair cable, a coaxial cable, and an optical fiber cable, and other wired communication techniques that are well known to those of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 illustrated in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various communication methods that are well known to those of ordinary skill in the art.

Figure 2:
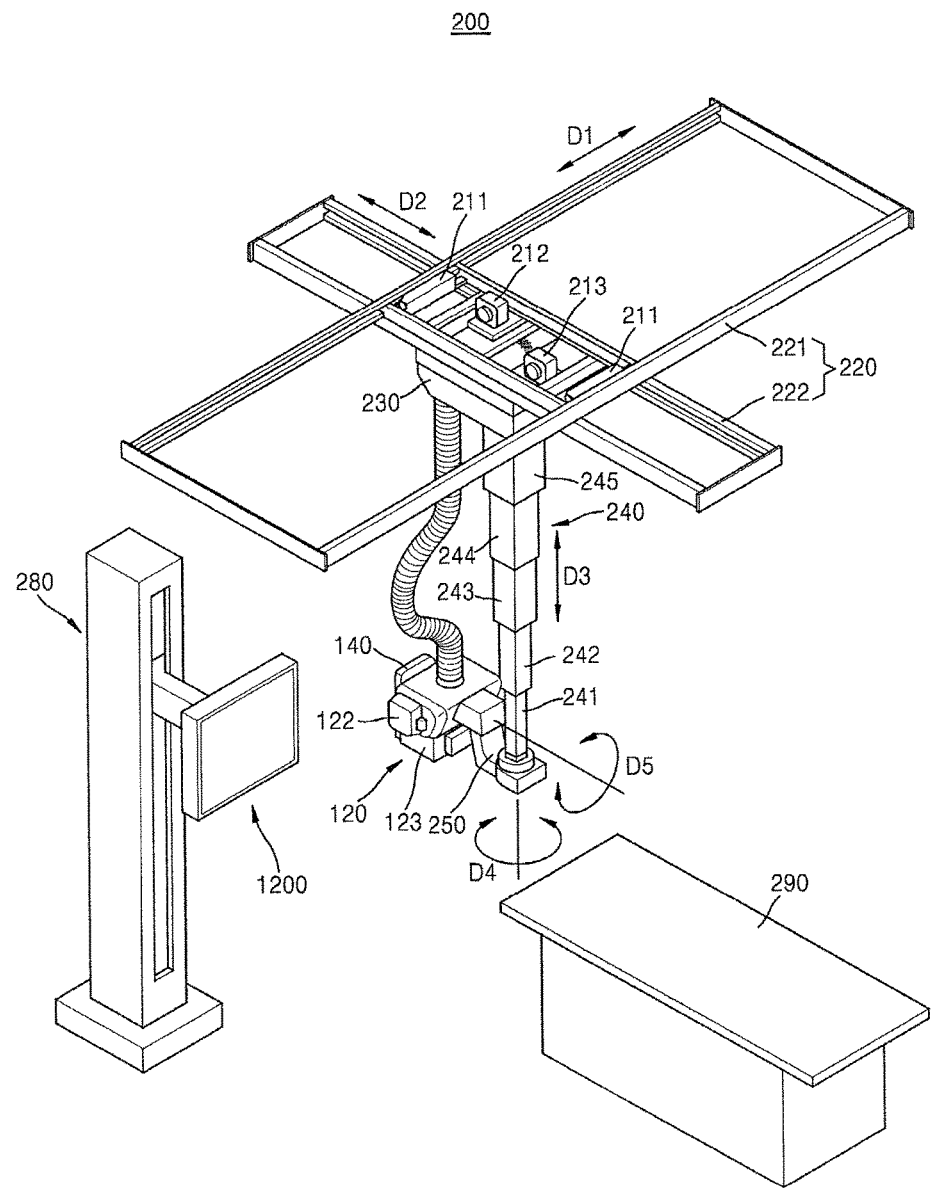
FIG. 2 is a perspective view of a fixed-type X-ray apparatus.

FIG. 2 is a perspective view of a fixed-type X-ray apparatus 200 according to an exemplary embodiment. The fixed-type X-ray apparatus 200 may be another exemplary embodiment of the X-ray apparatus 100 of FIG. 1. Components included in the fixed-type X-ray apparatus 200 that are the same as those of the X-ray apparatus 100 of FIG. 1 use the same reference numerals, and repeated descriptions thereof will be omitted.

Referring to FIG. 2, the fixed-type X-ray apparatus 200 includes an operation unit 140 providing a user with an interface for operating the X-ray apparatus 200, an X-ray irradiating unit 120 irradiating an X-ray to an object, a detection unit 130 detecting an X-ray that has passed through the object, first, second, and third motors 211, 212, and 213 providing a driving power to transport the X-ray irradiating unit 120, a guide rail 220, a moving carriage 230, and a post frame 240. The guide rail 220, the moving carriage 230, and the post frame 240 are formed to transport the X-ray irradiating unit 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not illustrated) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not illustrated) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detection unit 130 detects the X-ray that has passed through the object, and may be combined with a table-type receptor 290 or a stand-type receptor 280.

A rotating joint 250 is disposed between the X-ray irradiating unit 120 and the post frame 240. The rotating joint 250 allows the X-ray irradiating unit 120 to be coupled to the post frame 240, and supports a load applied to the X-ray irradiating unit 120.

The X-ray irradiating unit 120 connected to the rotating joint 250 may rotate on a plane that is perpendicular to the third direction D3. In this case, a rotating direction of the X-ray irradiating unit 120 may be defined as a fourth direction D4.

Also, the X-ray irradiating unit 120 may be configured to be rotatable on a plane perpendicular to the ceiling of the examination room. Therefore, the X-ray irradiating unit 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray irradiating unit 120 in the first, second, and third directions D1, D2, and D3. The first, second, and third motors 211, 212, and 213 may be electrically driven, and the first, second, and third motors 211, 212, and 213 may each include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a driving power transfer unit (not illustrated) so as to linearly move the X-ray irradiating unit 120 in the first, second, and third directions D1, D2, and D3. The driving power transfer unit may be a combination of a belt and a pulley, a combination of a chain and a sprocket, or a shaft, which are generally used.

As another example, motors (not illustrated) may be disposed between the rotating joint 250 and the post frame 240 and between the rotating joint 250 and the X-ray irradiating unit 120 in order to rotate the X-ray irradiating unit 120 in the fourth and fifth directions D4 and D5.

The operation unit 140 may be disposed on a side surface of the X-ray irradiating unit 120, but exemplary embodiments are not limited thereto. For example, the operation unit 140 may be included in the X-ray apparatus 200, or may be included in the workstation 110 connected to the X-ray apparatus 200.

Although FIG. 2 illustrates the fixed-type X-ray apparatus 200 connected to the ceiling of the examination room, the fixed-type X-ray apparatus 200 is merely an example for convenience of comprehension. That is, X-ray apparatuses according to exemplary embodiments may include X-ray apparatuses having various structures that are well known to those of ordinary skill in the art, for example, a C-arm-type X-ray apparatus, an angiography X-ray apparatus, and a mammography X-ray apparatus, in addition to the fixed-type X-ray apparatus 200 of FIG. 2.

The mammography X-ray apparatus will be described in detail with reference to FIG. 3.

The fixed-type X-ray apparatus 200 may perform X-ray photographing regardless of photographing places by including wheels for movement of the fixed-type X-ray apparatus 200.

Figure 3:
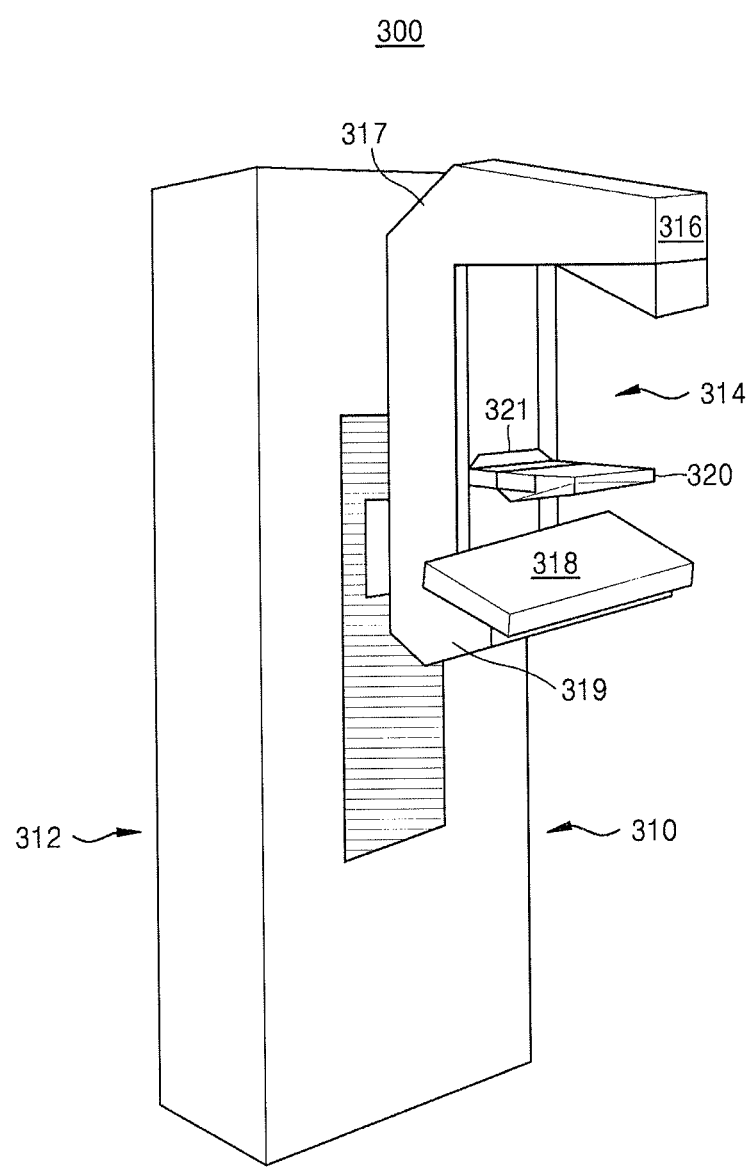
FIG. 3 is a perspective view of a mammography X-ray apparatus according to an exemplary embodiment.

FIG. 3 is a perspective view of a mammography X-ray apparatus 300 according to an exemplary embodiment. Referring to FIG. 3, the mammography X-ray apparatus 300 may include: a base 312; an imaging arm 314 attached to the base 312; an X-ray source 316 fixed to a top portion 317 of the imaging arm 314; a detection unit 318 fixed to a bottom portion 319 of the imaging arm 314; a compression paddle 320; and a compression paddle support 321. Although not illustrated in FIG. 3, the mammography X-ray apparatus 300 may further include an input unit and/or an output unit at the base 312 or the imaging arm 314. However, the position of the input unit or the output unit is not limited thereto. The detection unit 318 of FIG. 3 may correspond to the detection unit 130 of FIG. 1. The X-ray source 316 of FIG. 3 may correspond to the X-ray source 122 of FIG. 1.

The compression paddle 320 may be configured to press or compress a breast of the patient. When the object is pressed, since the X-ray exposure time of the object may be reduced, the X-ray irradiation dose may be reduced. Also, since the tissue structures overlapping with each other due to the pressing may be separated from each other, a clear image of a confused tissue structure may be acquired. In the mammography X-ray apparatus 300, the compression paddle 320 may be operated mechanically or by the user.

Figure 4:
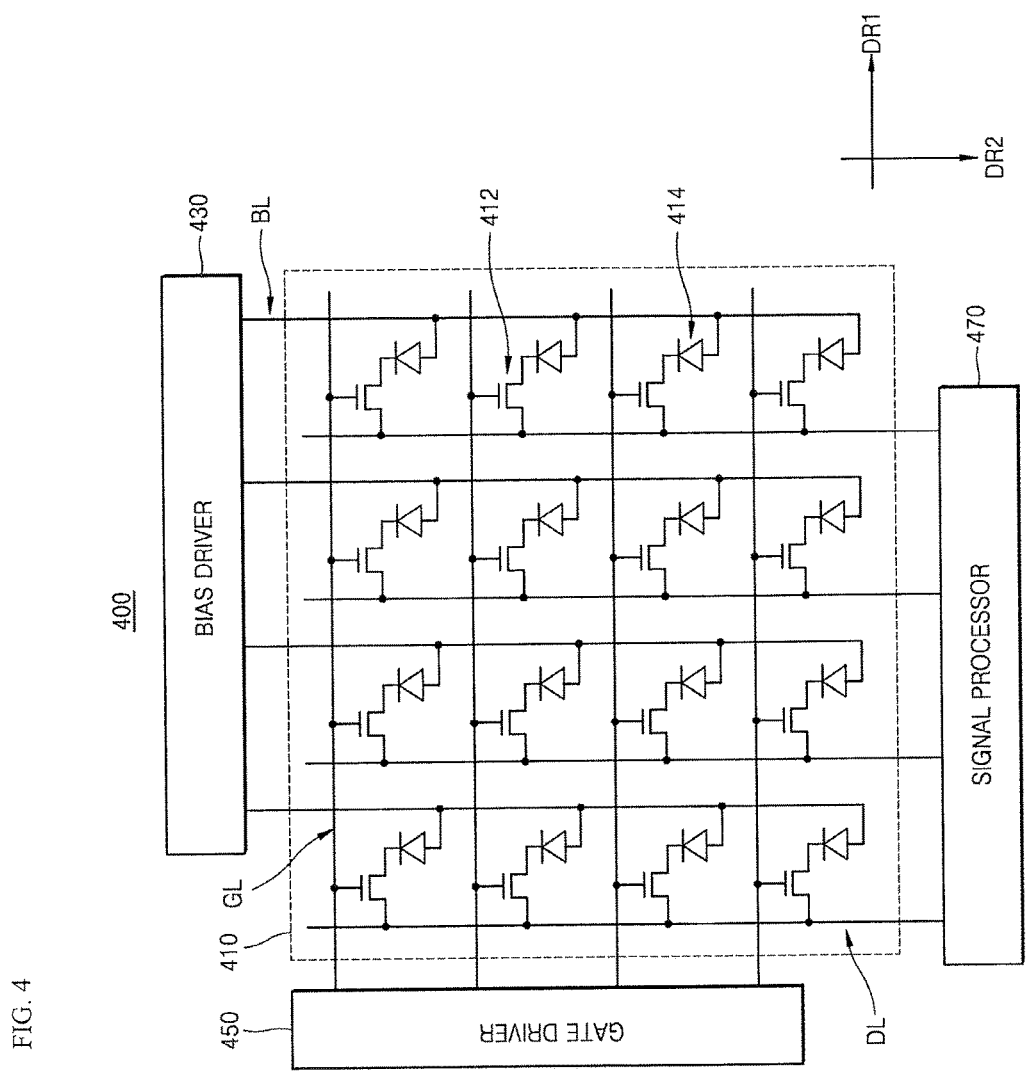
FIG. 4 is a diagram illustrating a detailed configuration of a detection unit according to an exemplary embodiment.

FIG. 4 is a diagram illustrating a detailed configuration of a detection unit 400 according to an exemplary embodiment. The detection unit 400 may be an exemplary embodiment of the detection unit 130 of FIGS. 1 to 3. The detection unit 400 may be an indirect-type detection unit.

Referring to FIG. 4, the detection unit 400 may include a scintillator (not illustrated), a photodetector substrate 410, a bias driving unit 430, a gate driving unit 450, and a signal processing unit 470.

The scintillator receives an X-ray irradiated from the X-ray source 122 and converts the X-ray into light.

The photodetector substrate 410 receives the light from the scintillator and converts the light into an electrical signal. The photodetector substrate 410 may include gate lines GL, data lines DL, TFTs 412, photodiodes 414, and bias lines BL.

The gate lines GL may be formed in the first direction DR1, and the data lines DL may be formed in the second direction DR2 that crosses the first direction DR1. The first direction DR1 and the second direction DR2 may intersect perpendicularly to each other. FIG. 4 illustrates four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 array) are illustrated as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 illustrates sixteen photodiodes 414 (in a 4×4 array) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 so as to be electrically connected to the photodiodes 414. FIG. 4 illustrates four bias lines BL formed along the second direction DR2 as an example.

The bias driving unit 430 is electrically connected to the bias lines BL so as to apply a driving voltage to the bias lines BL. The bias driving unit 430 may selectively apply a reverse bias voltage or a forward bias voltage to the photodiodes 414. A reference voltage may be applied to the N-side electrodes of the photodiodes 414. The reference voltage may be applied through the signal processing unit 470. The bias driving unit 430 may apply a voltage that is less than the reference voltage to the P-side electrodes of the photodiodes 414 so as to apply a reverse bias voltage to the photodiodes 414. On the other hand, the bias driving unit 430 may apply a voltage that is greater than the reference voltage to the P-side electrodes of the photodiodes 414 so as to apply a forward bias voltage to the photodiodes 414.

The gate driving unit 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processing unit 470 is electrically connected to the data lines DL. When the light received by the photodetector substrate 410 is converted into the electrical signal, the electrical signal may be read out by the signal processing unit 470 through the data lines DL.

An operation of the detection unit 400 will now be described. During the operation of the detection unit 400, the bias driving unit 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray.

Then, the gate driving unit 450 may sequentially apply the gate signals to the gate lines GL along the second direction DR2. When a gate signal is applied to a gate line GL and thus TFTs 412 connected to the gate line GL are turned on, photocurrents may flow into the signal processing unit 470 through the data lines DL due to the electric charges accumulated in the photodiodes 414 connected to the turned-on TFTs 412.

The signal processing unit 470 may convert the received photocurrents into image data. The signal processing unit 470 may output the image data to the outside. The image data may be in the form of an analog signal or a digital signal corresponding to the photocurrents.

Although not illustrated in FIG. 4, if the detection unit 400 illustrated in FIG. 4 is a wireless detection unit, the detection unit 400 may further include a battery unit and a wireless communication interface unit.

Figure 5:
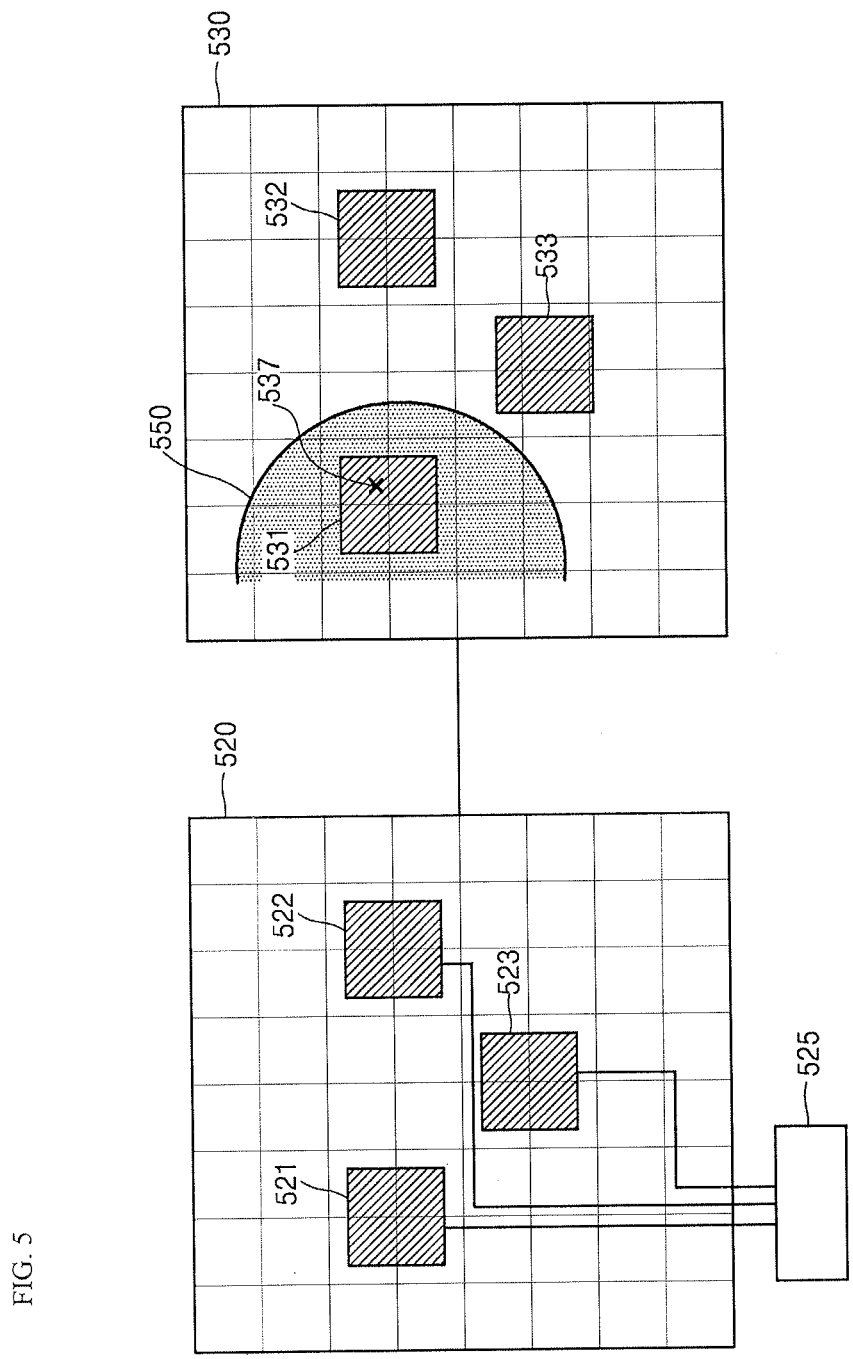
FIG. 5 is a diagram illustrating an auto exposure control (AEC) field according to an exemplary embodiment.

FIG. 5 is a diagram illustrating an auto exposure control (AEC) field according to an exemplary embodiment.

Referring to FIG. 5, a photodetector substrate 520 may correspond to the photodetector substrate 410. The photodetector substrate 520 may include a plurality of AEC field regions 521, 522, and 523. A signal processing unit 525 receives photocurrents from the AEC field regions 521, 522, and 523. Although three AEC field regions are illustrated in FIG. 5, the number of AEC field regions is not limited thereto.

An AEC may use an AEC field or a physically thin detector referred to as an AEC detector. In general, the AEC may be a portion of a photodetector substrate or may be attached to a photodetector substrate. First image information detected by the photodetector substrate 520 detected in the AEC field may be reconstructed as a first image 530 corresponding to a pre-shot image. Referring to FIG. 5, the first image 530 includes an effective AEC field 531 corresponding to a breast region 550. A density reference point 537 may be selected on the basis of a pixel value of the effective AEC field 531, and a density of an object (e.g., a breast) may be determined on the basis of the density reference point 537 of the effective AEC field 531.

In detail, the density of the object may be determined on the basis of the pixel value of an effective AEC field corresponding to a predetermined region (e.g., a breast region) of the object in the first image information. Here, the AEC field regions 521, 522, and 523 may correspond to a portion of the photodetector substrate 410 of FIG. 4 that is included in the detection unit 400 to detect a pixel value. That is, the photodetector substrate 410 may include a plurality of AEC fields. The effective AEC field may be one of the AEC fields that corresponds to a predetermined region of the object that the user desires to measure. For example, in mammography, when five effective AEC fields among a total of seven AEC fields correspond to the breast of the patient, the density of the object may be the lowest pixel value among the pixel values corresponding to the five effective AEC fields. Since the lowest pixel value means that the fewest X-rays have penetrated the object and then has reached the detector, it may mean that the corresponding part has the highest density. In this way, the density of the object may be determined by the lowest pixel value. However, this is merely exemplary, and the density of the object may be determined by the average of the pixel values of the effective AEC fields or by other calculation methods.

Figure 6:
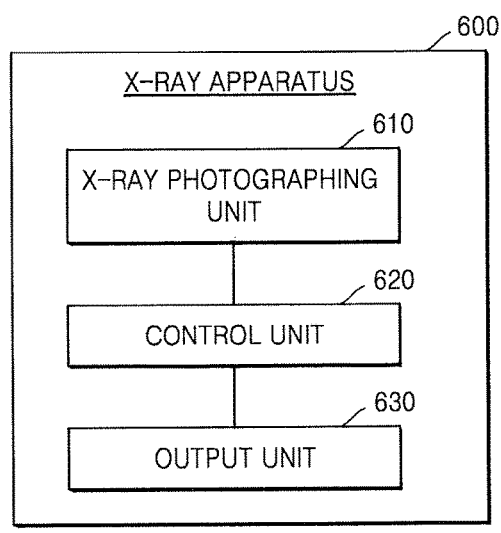
FIG. 6 is a block diagram of an X-ray apparatus according to an exemplary embodiment.

FIG. 6 is a block diagram of an X-ray apparatus 600 according to an exemplary embodiment.

Referring to FIG. 6, the X-ray apparatus 600 includes an X-ray photographing unit 610, a control unit 620, and an output unit 630.

The X-ray photographing unit 610 acquires X-ray image information of an object by X-ray photographing the object. The X-ray photographing unit 610 of FIG. 6 may correspond to the X-ray irradiating unit 120 of FIG. 1. Also, the X-ray apparatus 600 may be controlled by the workstation 110 of FIG. 1.

The X-ray apparatus 600 includes the X-ray photographing unit 610, the control unit 620, and the output unit 630. The X-ray photographing unit 610 acquires the first image information by irradiating an X-ray of a first dose to the object. The first image information may represent a pre-shot image for acquiring brief information of the object, and the pre-shot image may refer to an image for acquiring summary image information before capturing a main-shot image of the object. The X-ray of the first dose may be a relatively small X-ray for acquiring a pre-shot image of the object.

The control unit 620 determines the existence/nonexistence of a density abnormality of the object on the basis of the first image information.

The existence/nonexistence of the density abnormality of the object may be determined by comparing the density of the object with a predetermined reference value. For example, when the density of the object is not a value between a lower-limit threshold value and an upper-limit threshold value that are predefined by the X-ray apparatus 600, it may be determined as the density abnormality. For example, when the lower-limit threshold value is −50% determined by the user and a density error rate is −70%, or when the upper-limit threshold value is +150% determined by the user and the density error rate is +700%, it may be determined as the density abnormality. Here, the density error rate may represent the degree of difference between a reference density and the density of the object. For example, when the density of the object is twice the reference density, the density error rate may be +100%, and when the density of the object is half the reference density, the density error rate may be −50%.

The output unit 630 displays information about the existence/nonexistence of the density abnormality. In detail, the output unit 630 may include a display and a speaker, and may display the information about the existence/nonexistence of the density abnormality by a picture or a sound through the display or the speaker. For example, when the density abnormality exists, the output unit 630 may output a message indicating the density abnormality on the display. Also, the output unit 630 may output a degree of the density abnormality and/or a type of the density abnormality as a message on the display. Also, the output unit 630 may display at least one of information about the density abnormality existence/nonexistence, the density abnormality degree, and the density abnormality type together with a first image acquired on the basis of the first image information. This will be described later in detail with reference to FIGS. 11 and 12.

Also, the output unit 630 may output an alarm indicating the density abnormality. The alarm indicating the density abnormality may include a sound. The output unit 630 may generate a sound indicating information about the density abnormality existence/nonexistence and may also generate a sound indicating the density abnormality degree and/or the density abnormality type.

Hereinafter, X-ray apparatuses according to some other exemplary embodiments will be described in detail with reference to FIGS. 7 to 12.

Figure 7:
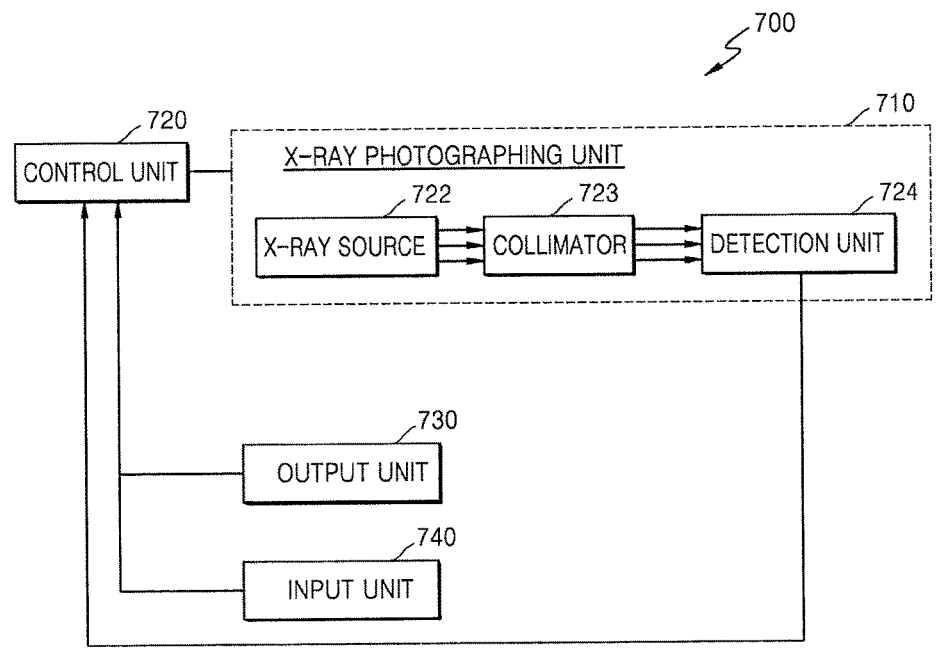
FIG. 7 is a block diagram of an X-ray apparatus according to an exemplary embodiment.

FIG. 7 is a block diagram of an X-ray apparatus 700 according to an exemplary embodiment.

Referring to FIG. 7, the X-ray apparatus 700 may include an X-ray photographing unit 710, a control unit 720, an output unit 730, and an input unit 740. The X-ray photographing unit 710, the control unit 720, and the output unit 730 of FIG. 7 may correspond to the X-ray photographing unit 610, the control unit 620, and the output unit 630 of FIG. 6, and redundant descriptions thereof may be omitted for conciseness. The X-ray photographing unit 710 may include an X-ray source 722, a collimator 723, and a detection unit 724.

The input unit 740 may receive an input about rephotographing of the first image information from the user. For example, the user may see a screen displaying information about the existence/nonexistence of the density abnormality related to the first image information and request rephotographing of the first image information through the input unit 740. Also, the user may directly check the first image and request the rephotographing through the input unit 740, or may recognize the density abnormality of the object through a picture or a sound output by the output unit 730 and request the rephotographing through the input unit 740.

When a pre-shot rephotographing request is not input through the input unit 740, the X-ray photographing unit 710 may acquire second image information by irradiating an X-ray of a second dose, which is greater than the first dose, to the object. The irradiation dose of the X-ray of the first dose and the irradiation dose of the X-ray of the second dose will be described later with reference to FIG. 13. The first image information may correspond to a pre-shot image for schematically observing the object, and the second image information may correspond to a main-shot image of the object that the user actually desires to acquire.

When a pre-shot rephotographing request is input through the input unit 740, the X-ray photographing unit 710 may reacquire the first image information by re-irradiating the X-ray of the first dose to the object. When pre-shot rephotographing is requested, the object may be repositioned. The repositioning of the object may mean adjustment of the position of the object, modification of setting values for an implant patient, elimination of a collimator operation error, and elimination of a filter operation error. That is, the repositioning of the object may mean eliminating a problem appearing in the first image corresponding to the first image information and then preparing to recapture the first image.

According to another exemplary embodiment, even if pre-shot rephotographing is not requested, when a main-shot image is not requested by the user, the X-ray apparatus 700 may determine the need for pre-shot rephotographing and perform the pre-shot rephotographing. According to another exemplary embodiment, when a main-shot image is not requested by the user for a predetermined time, the X-ray apparatus 700 may determine the need for pre-shot rephotographing and perform the pre-shot rephotographing.

According to some exemplary embodiments, a value of the X-ray of the second dose corresponding to a main shot is input through the input unit 740, the X-ray photographing unit 710 may acquire main image information corresponding to the second image information by irradiating the X-ray of the second dose.

The output unit 730 may further display the degree of the density abnormality based on the density of the object. For example, the degree of the density abnormality may represent the density error rate of the object based on the reference density. For example, when the density of the object is twice the reference density, the density error rate may be +100%, and when the density of the object is half the reference density, the density error rate may be −50%. However, this calculation is merely exemplary, and exemplary embodiments are not limited thereto.

The output unit 730 may further display the density abnormality type based on the density of the object. Examples of the density abnormality type may include a setting error in the implant patient, a collimator operation error, and a filter operation error. This will be described later in detail with reference to FIGS. 15A to 15C.

Figure 8:
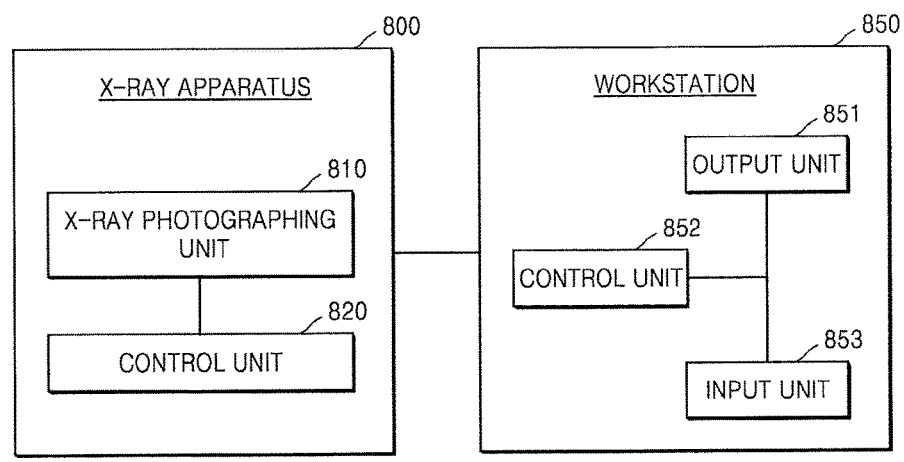
FIG. 8 is a block diagram illustrating an X-ray apparatus and a workstation configured to control the X-ray apparatus according to an exemplary embodiment.

FIG. 8 is a block diagram illustrating an X-ray apparatus 800 and a workstation 850 configured to control the X-ray apparatus 800 according to an exemplary embodiment.

The X-ray apparatus 800 may include an X-ray photographing unit 810 and a control unit 820. The workstation 850 may include an output unit 851, a control unit 852, and an input unit 853.

The X-ray photographing unit 810 acquires first image information by irradiating an X-ray of a first dose to the object. The control unit 820 of the X-ray apparatus 800 controls the X-ray photographing unit 810. The control unit 852 of the workstation 850 receives the first image information, which is acquired by irradiating the X-ray of the first dose to the object, from the X-ray apparatus 800 and determines the existence/nonexistence of the density abnormality of the object on the basis of the received first image information. The output unit 851 displays information about the existence/nonexistence of the density abnormality. The X-ray apparatus 800 may be controlled by the workstation 850 and may perform an input/output operation through the workstation 850.

Figure 9:
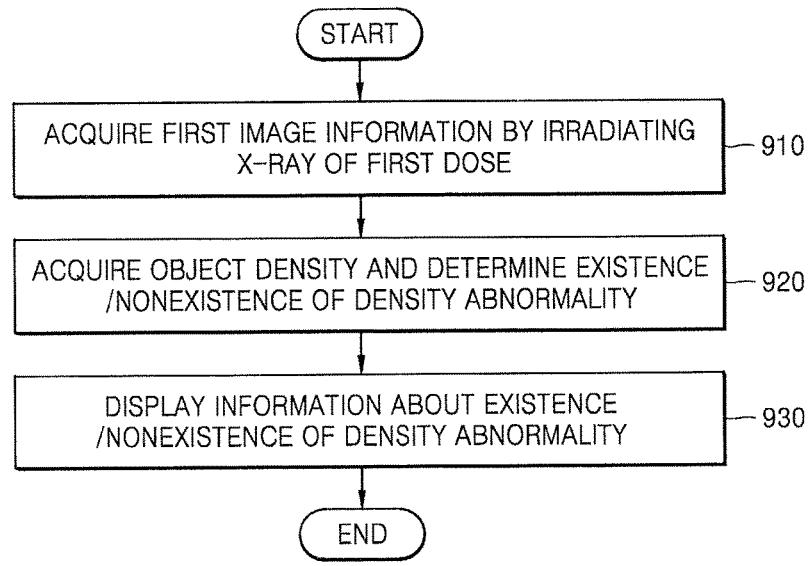
FIG. 9 is a flowchart of a method of controlling an X-ray apparatus according to an exemplary embodiment.

FIG. 9 is a flowchart of a method of controlling an X-ray apparatus according to an exemplary embodiment.

Referring to FIG. 9, in operation 910, the X-ray apparatus acquires first image information by irradiating an X-ray of a first dose to the object. In operation 920, the X-ray apparatus determines the existence/nonexistence of a density abnormality of the object on the basis of the first image information. In operation 930, the X-ray apparatus displays information about the existence/nonexistence of the density abnormality. Since the operations of the X-ray apparatus have already been described in detail with reference to FIGS. 6 and 7, redundant descriptions thereof will be omitted for conciseness.

Figure 10:
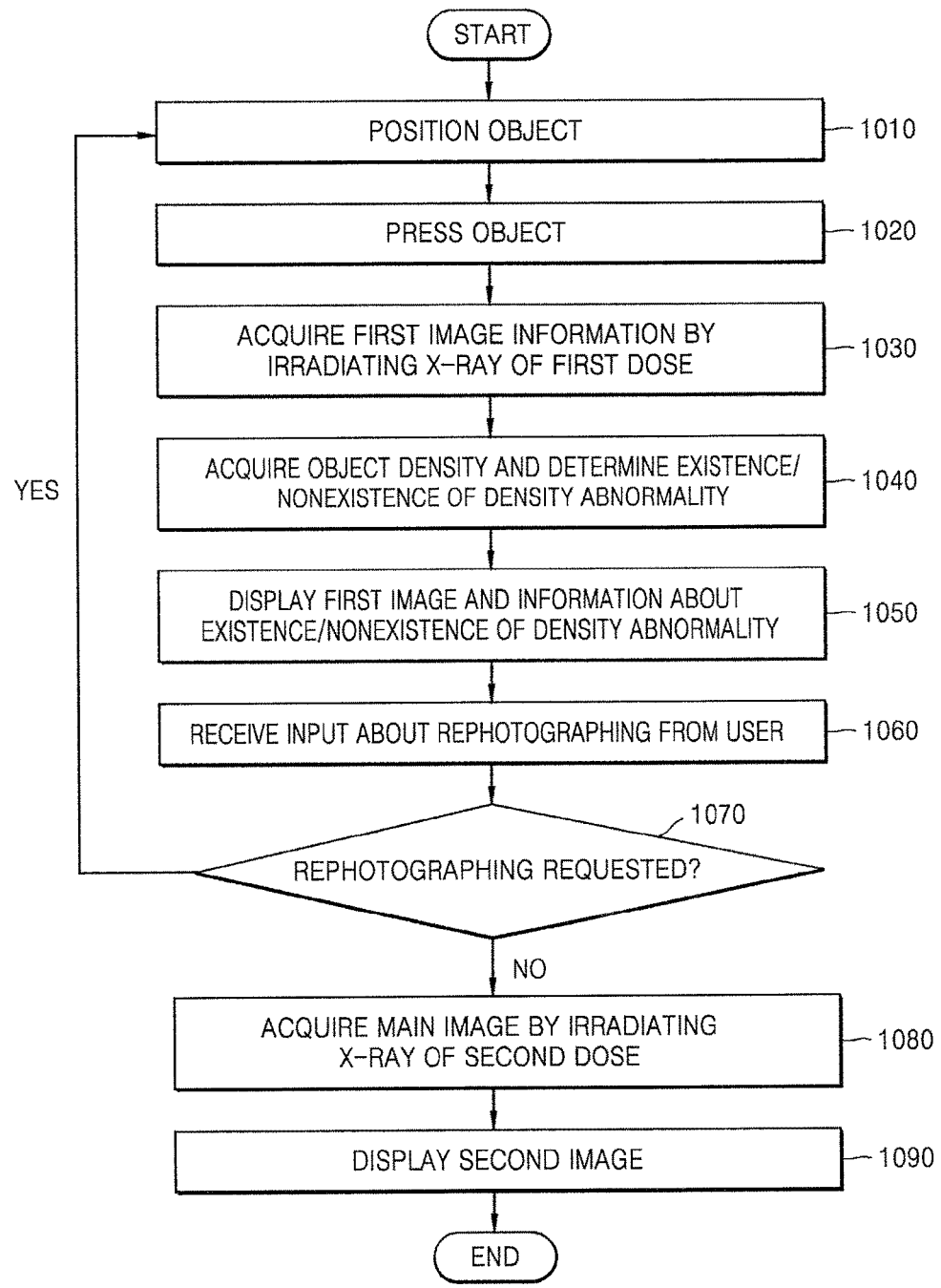
FIG. 10 is a flowchart of a method of controlling an X-ray apparatus according to an exemplary embodiment.

FIG. 10 is a flowchart of a method of controlling an X-ray apparatus according to an exemplary embodiment.

In operation 1010, the object may be positioned on the X-ray apparatus. That the object is positioned on the X-ray apparatus may mean that the object is located on the detection unit of the X-ray apparatus so that the X-ray apparatus may photograph the object.

In operation 1020, the X-ray apparatus may press the object. For example, when the object is a breast, the compression paddle included in the X-ray apparatus may press the breast. This pressing may be performed in mammography for medically examining a breast cancer. When the object is pressed, since the X-ray exposure time of the object may be reduced, the X-ray irradiation dose may be reduced. Also, since the tissue structures overlapping with each other due to the pressing may be separated from each other, a confused tissue structure image may be clearly acquired.

In operation 1030, the X-ray apparatus acquires first image information by irradiating an X-ray of a first dose to the object. In operation 1040, the X-ray apparatus calculates the density of the object and determines the existence/nonexistence of a density abnormality of the object. In operation 1050, the X-ray apparatus displays the first image and the information about the existence/nonexistence of the density abnormality. Since operations 1030 to 1050 correspond to operations 910 to 930, redundant descriptions thereof will be omitted for conciseness.

In operation 1060, the X-ray apparatus receives an input about rephotographing from the user. For example, the X-ray apparatus may receive a rephotographing request from the user through the keyboard, the mouse, the touchscreen, or the voice recognizer included in the X-ray apparatus.

In operation 1070, the X-ray apparatus determines whether rephotographing is requested. When rephotographing is not requested, the X-ray apparatus proceeds to operation 1080. In operation 1080, the X-ray apparatus acquires a second image by irradiating a second X-ray to the object. On the other hand, when rephotographing is requested, the X-ray apparatus returns to operation 1010 and repositions the object. The second image may refer to a main image of the object that the user desires to acquire in the result. The repositioning of the object may mean adjustment of the position of the object, modification of setting values for an implant patient, elimination of a collimator operation error, and elimination of a filter operation error. That is, the repositioning of the object may mean eliminating a problem appearing in the first image and then preparing to recapture the first image. Also, according to some exemplary embodiments, even when the user does not request rephotographing, the X-ray apparatus may return to operation 1010 and perform rephotographing according to the determination based on the density information of the object.

In operation 1090, the X-ray apparatus may display the second image. That is, the X-ray apparatus may display the second image, which is acquired by irradiating the second X-ray to the object, on the screen.

FIGS. 11A to 11D are diagrams illustrating an interface for an output unit of an X-ray apparatus according to an exemplary embodiment.

The output unit of the X-ray apparatus may include a display, and FIGS. 11A to 11D may be applied not only to the output unit of the X-ray apparatus but also to the output unit of the workstation.

Figure 11A:
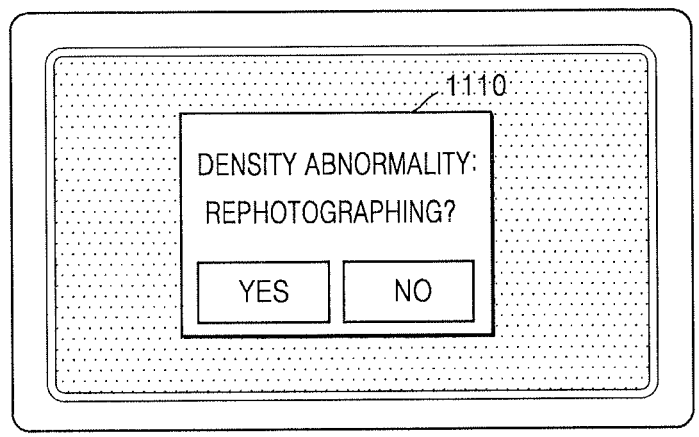
FIGS. 11A to 11D are diagrams illustrating an interface for an output unit of an X-ray apparatus according to an exemplary embodiment.

Referring to FIG. 11A, a message 1110 for inquiring about rephotographing and an indication of the density abnormality existence/nonexistence may be displayed on the display. Also, according to another exemplary embodiment, the indication of the density abnormality existence/nonexistence may be notified by a sound through the output unit 630.

Figure 11B:
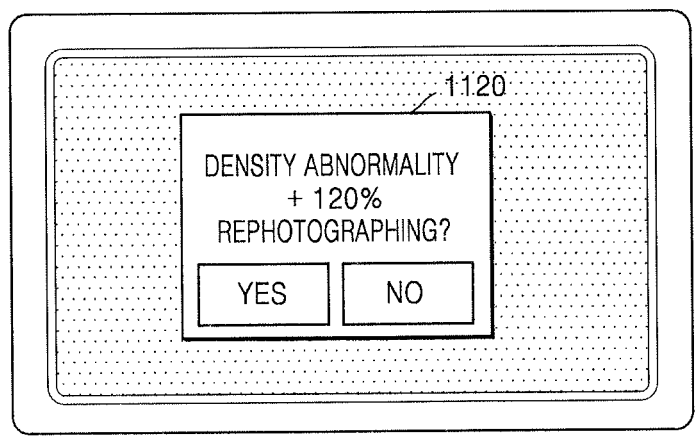

Referring to FIG. 11B, a message 1120 for inquiring about rephotographing and an indication of the density abnormality degree may be displayed on the display. For example, the density abnormality degree may represent the density error rate based on the reference density. The density abnormality degree may be displayed by a text on the screen, or may be notified by a sound through the output unit 630.

Figure 11C:
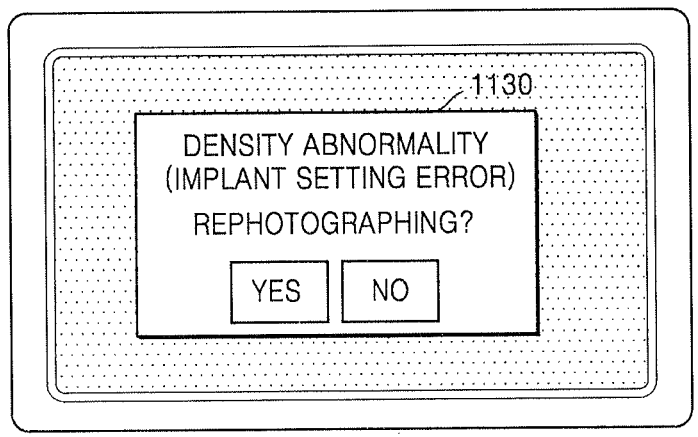

Referring to FIG. 11C, a message 1130 for inquiring about rephotographing and an indication of the density abnormality type may be displayed on the display. Examples of the density abnormality type may include a setting error in the implant patient, a collimator operation error, and a filter operation error. This will be described later in detail with reference to FIGS. 15A to 15C.

Figure 11D:
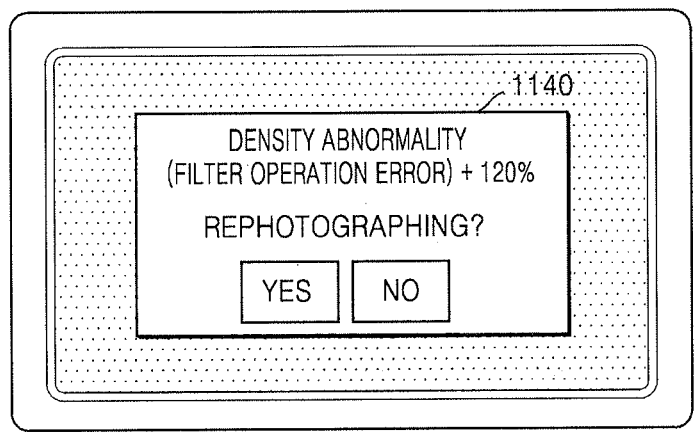

Referring to FIG. 11D, a message 1140 for inquiring about rephotographing, the density abnormality type, and the density abnormality degree may be displayed on the display. This screen configuration is merely exemplary, and the X-ray apparatus may notify information about the density abnormality by various other screen configurations. Also, according to other exemplary embodiments, in addition to being displayed on the screen, the information about the density abnormality may be notified by a sound through the output unit 630 or may be notified to the user by using a picture and a sound simultaneously.

FIGS. 12A to 12D are diagrams illustrating an interface for an output unit of an X-ray apparatus according to an exemplary embodiment.

Figure 12A:
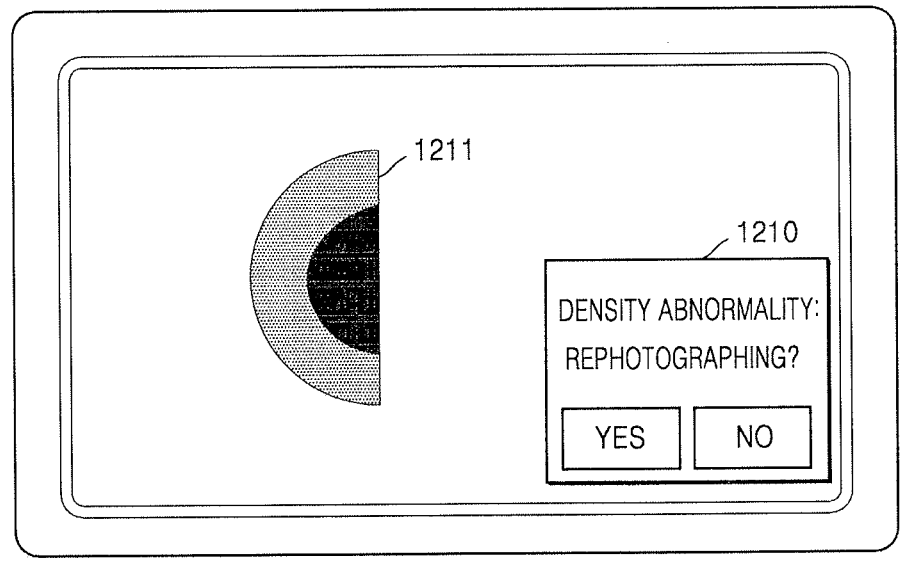
FIGS. 12A to 12D are diagrams illustrating an interface for an output unit of an X-ray apparatus according to an exemplary embodiment.

Referring to FIG. 12A, together with a first image 1211, a message 1210 for inquiring about rephotographing and an indication of the density abnormality existence/nonexistence may be displayed on the display. Also, according to another exemplary embodiment, instead of being displayed on the screen, the indication of the density abnormality existence/nonexistence may be notified by a sound through the output unit 630.

Figure 12B:
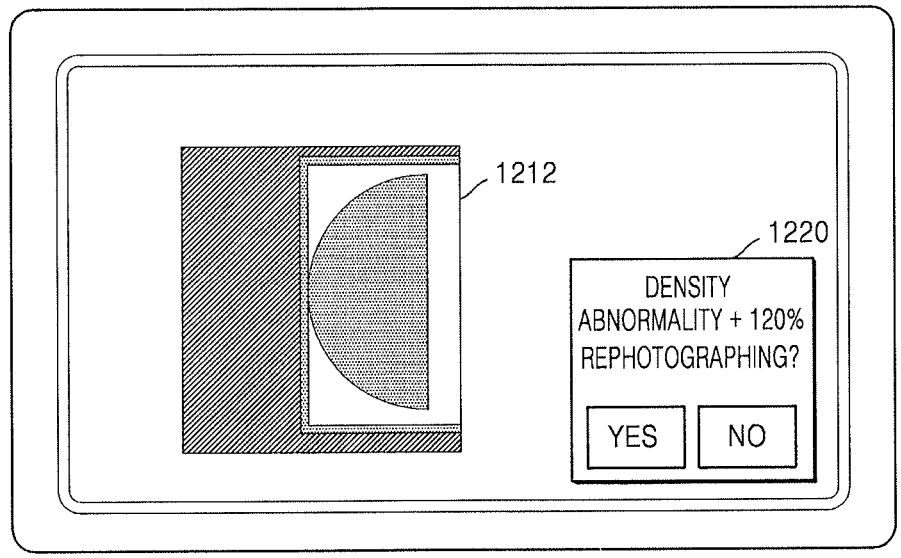

Referring to FIG. 12B, together with a first image 1212, a message 1220 for inquiring about rephotographing and an indication of the density abnormality degree may be displayed on the display. For example, the density abnormality degree may represent the density error rate based on the reference density.

Figure 12C:
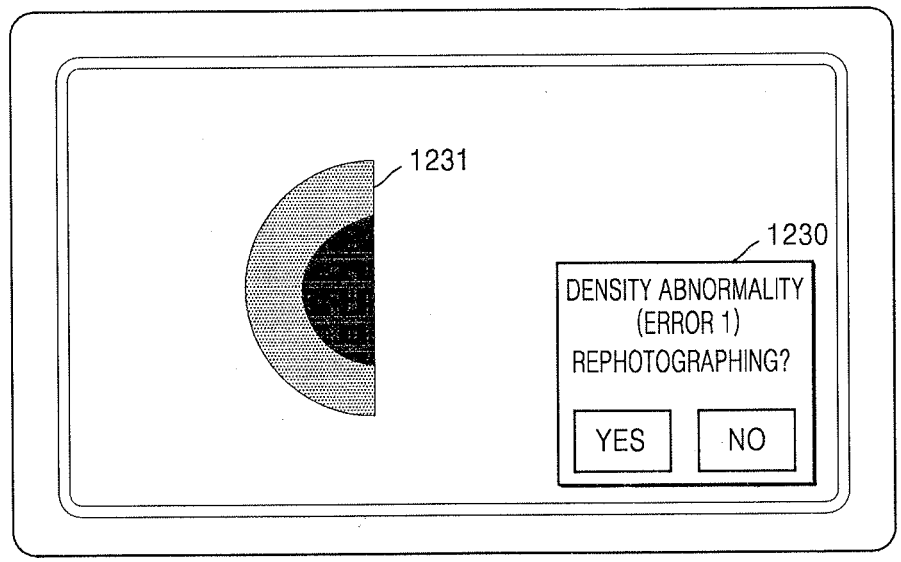

Referring to FIG. 12C, together with a first image 1231, a message 1230 for inquiring about rephotographing and an indication of the density abnormality type may be displayed on the display. Examples of the density abnormality type may include a setting error in the implant patient, a collimator operation error, and a filter operation error.

Figure 12D:
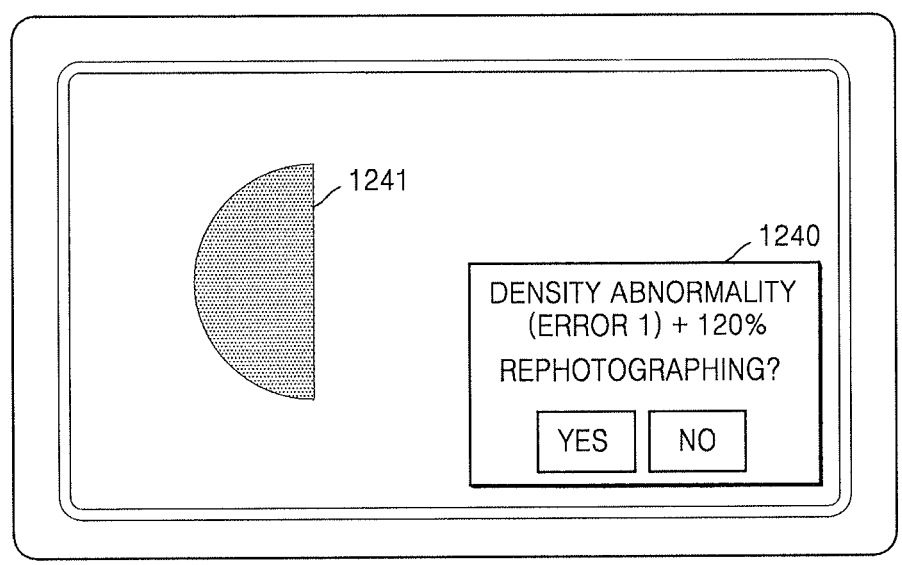

Referring to FIG. 12D, together with a first image 1241, a message 1240 for inquiring about rephotographing, the density abnormality type, and the density abnormality degree may be displayed on the display. This screen configuration is merely exemplary, and the X-ray apparatus may notify the user of information about the density abnormality by various other screen configurations. Also, according to other exemplary embodiments, in addition to displaying the information about the density abnormality on the screen, the X-ray apparatus may notify the user of the information about the density abnormality by using a sound through the output unit or by using a picture and a sound simultaneously.

The user may determine the necessity for rephotographing by synthesizing the information about the existence/nonexistence, type, and degree of the density abnormality and the first image displayed on the screen.

Figure 13:
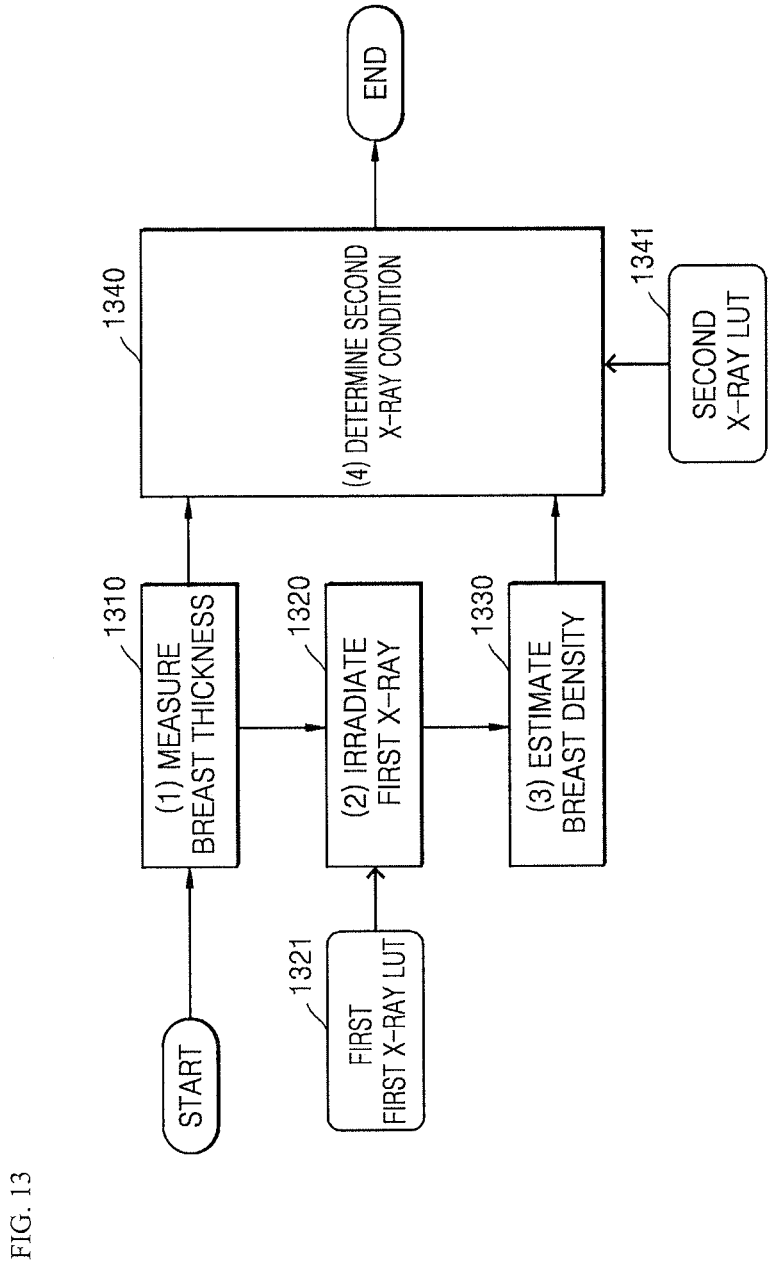
FIG. 13 is a diagram illustrating references for determining an X-ray of a first dose and an X-ray of a second dose in mammography according to an exemplary embodiment.

FIG. 13 is a diagram illustrating references for determining an X-ray of a first dose and an X-ray of a second dose in mammography according to an exemplary embodiment.

The X-ray of the first dose and the X-ray of the second dose may be determined by the control unit 820 of the X-ray apparatus 800 or the control unit 852 of the workstation 850.

*185In operation 1310, a breast thickness of the patient is measured. The breast thickness may be measured automatically by the X-ray apparatus or directly by the user.

In operation 1320, the X-ray of the first dose is irradiated on the basis of the measured breast thickness. The X-ray of the first dose may be determined corresponding to the patient breast thickness in a first X-ray lookup table (LUT) 1321. The first X-ray LUT 1321 may be a lookup table that indicates the X-ray of the optimal first dose corresponding to various breast thicknesses that are experimentally predetermined. The first X-ray LUT 1321 may be stored in a memory (not illustrated) of the X-ray apparatus and may be used by the control unit of the X-ray apparatus to acquire the X-ray of the first dose corresponding to the patient breast thickness.

In operation 1330, a breast density of the object is estimated. The object breast density may be estimated on the basis of the first image that is acquired by irradiating the first X-ray to the object. The estimation of the object breast density will be described later in detail with reference to FIG. 14.

In operation 1340, on the basis of the measured breast thickness and breast density, the X-ray of the second dose is determined and irradiated to the object. The X-ray of the second dose may be determined corresponding to the breast thickness and the breast density in a second X-ray LUT 1341. The second X-ray LUT 1341 may be a lookup table that indicates the X-ray of the optimal second dose corresponding to various breast thicknesses and breast densities that are experimentally predetermined. The second X-ray LUT 1341 may be stored in the memory (not illustrated) of the X-ray apparatus and may be used by the control unit of the X-ray apparatus to acquire the X-ray of the second dose corresponding to the breast thickness and the breast density of the patient. In the present exemplary embodiment, the first X-ray LUT 1321 and the second X-ray LUT 1341 may be stored in the memory of the X-ray apparatus. However, in another exemplary embodiment, the first X-ray LUT 1321 and the second X-ray LUT 1341 may be stored in the memory of the workstation.

Figure 14:
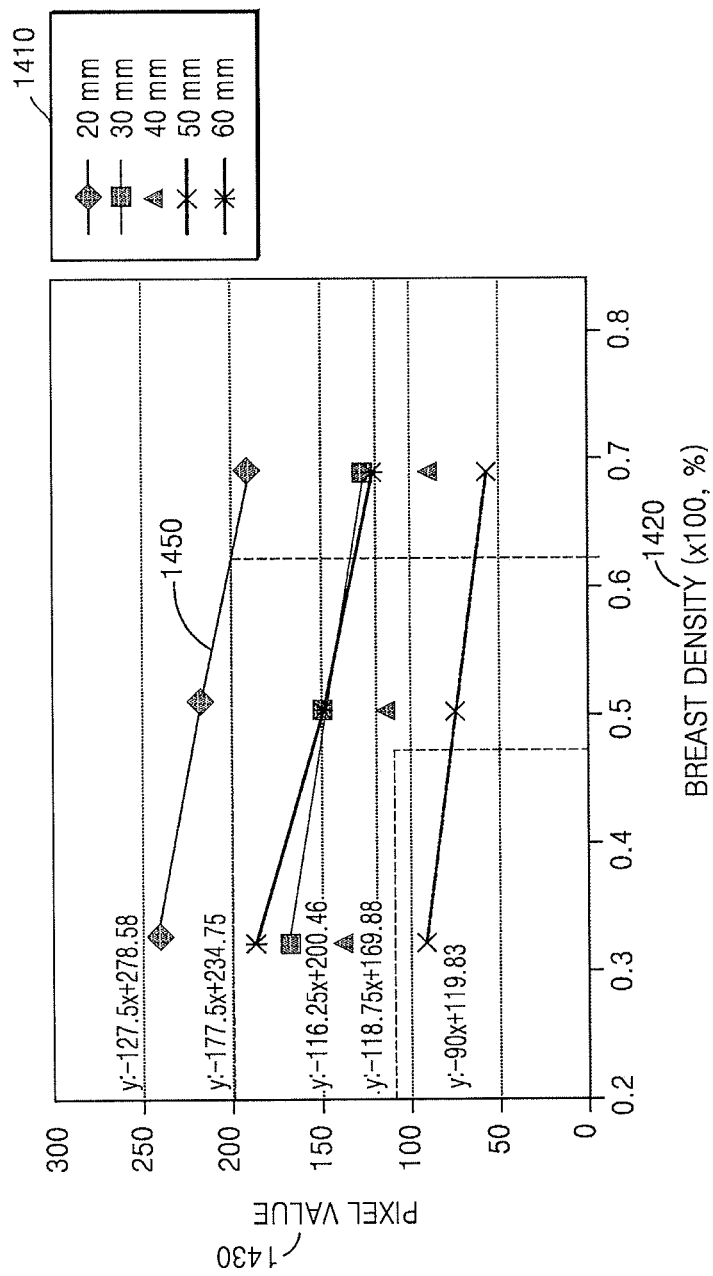
FIG. 14 is a graph for determining a breast density on the basis of pixel values according to an exemplary embodiment.

FIG. 14 is a graph for finding a breast density on the basis of pixel values according to an exemplary embodiment.

FIG. 14 illustrates a graph representing the relationship between a phantom thickness 1410, a pixel value 1430, and a breast density 1420. This graph is based on the values of a plurality of patients that are experimentally pre-measured. It may be seen from FIG. 14 that the relationship between the pixel value 1430 and the breast density 1420 varies according to the phantom thickness 1410. The phantom thickness 1410 may be determined on the basis of the breast thickness of the patient. Also, it may be seen that when the phantom thickness 1410 is fixed, the pixel value 1430 decreases as the breast density 1420 increases.

The X-ray apparatus may determine the phantom thickness 1410 according to the breast thickness of the patient, find a straight line 1450 of the graph corresponding to the relevant phantom thickness 1410, and find the breast density 1420 depending on the pixel value 1430.

For example, the X-ray apparatus detects a breast region in the first image and selects a region having the lowest pixel value in the effective AEC field corresponding to the breast region. The region having the lowest pixel value may be a region having the highest breast density. The density of the graph corresponding to the pixel value 1430 of the relevant region may be determined as the density of the object. For example, if the phantom thickness 1410 is 20 mm, when the pixel value 1430 is 200, the breast density 1420 may be determined as about 62%.

Figure 15A:
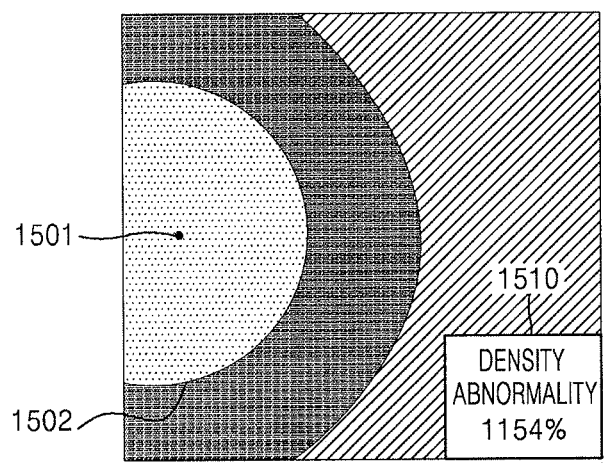
FIGS. 15A to 15C are diagrams illustrating density abnormality types as density abnormality factors.
Figure 15B:
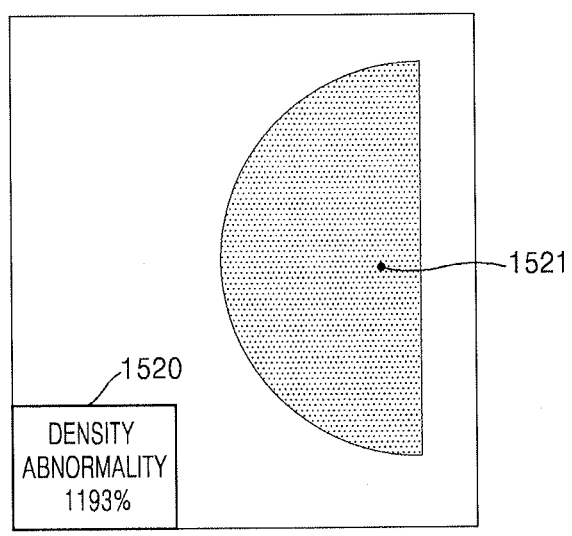
Figure 15C:
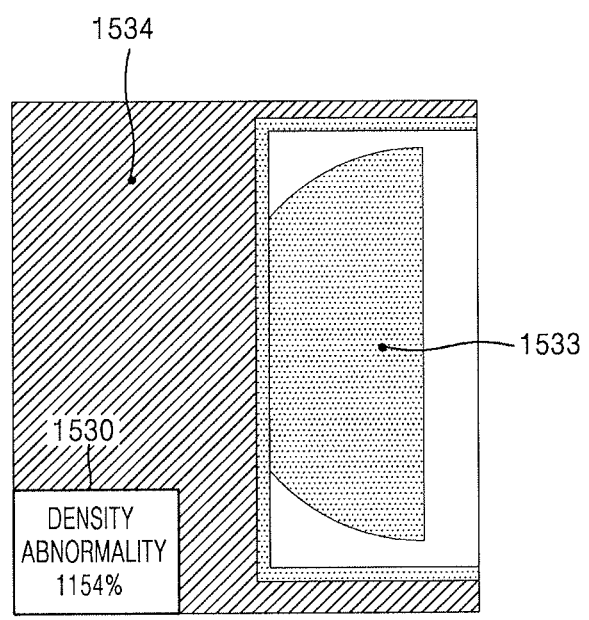

FIGS. 15A to 15C are diagrams illustrating density abnormality types as density abnormality factors. FIGS. 15A to 15C may correspond to a screen displaying a first image (i.e., a pre-shot image).

FIG. 15A illustrates the case of a density abnormality of the implant patient. While a density is measured at a density reference point 1501, since the density is measured erroneously due to an inserted implant 1502, a density error rate 1510 is illustrated as 1154%. Here, the density reference point 1501 refers to a point at which the density of the object is measured, and may be, for example, a point having the lowest pixel value in the region corresponding to the effective AEC field.

In order to determine whether the X-ray apparatus may detect a density abnormality of the implant patient, for example, when a phantom having a density of 50% and a thickness of 4 cm is placed on an AEC field region, a lead plate is placed on the phantom to cover a predetermined portion of the AEC field region, a paddle is compressed, and a pre-shot image is captured in an AEC mode, it may be determined whether a density abnormality indicating message is output.

FIG. 15B illustrates the case of a filter operation error. In the X-ray apparatus, a filter is located at a collimator to perform a filtering operation so that X-rays of different intensities are irradiated to the object. For example, when the thickness of the phantom varies, the type of the filer used varies, and when not a corresponding filter but another filter is used according to the thickness of the phantom, a filter error occurs. When a filter error exists, the density of the object may be measured erroneously. For example, while a collimator region error or an implant error does not exist in FIG. 15B, a density error rate 1520 is illustrated as 1193%, which may be caused by the filter operation error.

In order to determine whether the X-ray apparatus may detect a filter operation error, for example, when a phantom having a density of 50% and a thickness of 4 cm is placed on an AEC field region, a silver (Ag) or rhodium (Rh) filter is attached in front of the collimator to cover the entire irradiation region, the paddle is compressed, and a pre-shot image is captured in an AEC mode, it may be determined whether a density abnormality indicating message is output.

FIG. 15C illustrates the case of a collimator operation error. The collimator adjusts an X-ray irradiation region by guiding the path of an X-ray that is generated and irradiated by the X-ray source 122. However, when the X-ray irradiation region is designated erroneously due to the collimator operation error, the density of the object may be measured erroneously. In FIG. 15C, a density error rate 1530 is illustrated as 1154%.

In order to determine whether the X-ray apparatus may detect a collimator operation error, for example, when a phantom having a density of 50% and a thickness of 4 cm is placed on an AEC field region, a lead plate is attached in front of the collimator to cover the half of the detection unit, the paddle is compressed, and a pre-shot image is captured in an AEC mode, it may be determined whether a density abnormality indicating message is output.

In order to determine whether the X-ray apparatus may detect an error caused by a mistake of a radiologic technologist, for example, when a phantom having a density of 50% and a thickness of 4 cm is placed on an AEC field region, an AEC position is set outside the phantom, the paddle is compressed, and a pre-shot image is captured in an AEC mode, it may be determined whether a density abnormality indicating message is output.

As illustrated in FIGS. 15A to 15C, the density abnormality information and the pre-shot image may be displayed on a screen, and the user may clearly determine the necessity for rephotographing of a pre-shot image on the basis of the screen.

As described above, according to the one or more of the above exemplary embodiments, the X-ray apparatus may prevent the rephotographing of the second image caused by a system error (e.g., a collimator error or a filter error) on the basis of at least one of the pre-shot image, the alarm, and the message about the density abnormality. That is, since the user may recognize a system error that the user has difficulty in determining only by the pre-shot image (i.e., the first image), twice or more photographing of the second image requiring a large X-ray irradiation dose may be prevented. Also, the over-irradiation of the X-ray of the second dose caused by an unexpected implant insertion may be prevented.

The above exemplary embodiments may be written as a program and may be implemented in a general-purpose digital computer that executes the program by using a computer-readable recording medium.

Examples of the computer-readable recording medium include magnetic storage media (e.g., ROMs, floppy disks, hard disks, etc.), optical recording media (e.g., CD-ROMs, DVDs, etc.), and transmission media such as Internet transmission media.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

The invention claimed is:

1. An X-ray apparatus comprising:
   an X-ray photographing unit configured to acquire first image information by irradiating an X-ray of a first dose to an object;
   a control unit configured to determine existence/nonexistence of a density abnormality of the object on the basis of the first image information;
   an output unit configured to display information about the existence/nonexistence of the density abnormality; and
   an input unit configured to receive an input about rephotographing of the first image information from a user, wherein when the rephotographing is not requested in the input, the X-ray photographing unit further acquires second image information by irradiating an X-ray of a second dose greater than the first dose, and
   the second dose is determined on the basis of at least one of a measured object thickness and object density.

2. The X-ray apparatus of claim 1, wherein the control unit acquires a density of the object density from the first image information and compares the acquired object density with a predetermined reference value to determine the existence/nonexistence of the density abnormality.

3. The X-ray apparatus of claim 1, wherein the output unit further displays at least one of a degree and a type of the density abnormality based on the object density.

4. The X-ray apparatus of claim 1, wherein the control unit acquires the object density on the basis of pixel values of an effective auto exposure control (AEC) field corresponding to a predetermined region of the object in the first image information to determine the existence/nonexistence of the density abnormality.

5. The X-ray apparatus of claim 4, wherein when the acquired object density is a value between a lower-limit threshold value and an upper-limit threshold value, the control unit determines that the density abnormality does not exist.

6. The X-ray apparatus of claim 1, wherein the output unit outputs an alarm about the density abnormality, when the density abnormality exists, and
   wherein the output unit further displays a message about the existence/nonexistence of the density abnormality and a first image based on the first image information.

7. The X-ray apparatus of claim 1, wherein the X-ray photographing unit determines an irradiation dose of the X-ray of the second dose on the basis of the object density and irradiates the X-ray of the second dose according to the determined irradiation dose to acquire the second image information.

8. The X-ray apparatus of claim 4, wherein the object density is acquired on the basis of the lowest pixel value among the pixel values of the effective AEC field.

9. The X-ray apparatus of claim 1, wherein when the rephotographing is requested in the input, the X-ray photographing unit modifies the first image information by rephotographing the object.

10. The X-ray apparatus of claim 1, further comprising a compression paddle configured to compress the object.

11. A method of controlling an X-ray apparatus, the method comprising:
    acquiring first image information by irradiating an X-ray of a first dose to an object;
    determining existence/nonexistence of a density abnormality of the object on the basis of the first image information;
    displaying information about the existence/nonexistence of the density abnormality;
    receiving an input about rephotographing of the first image information from a user; and
    acquiring second image information by irradiating an X-ray of a second dose greater than the first dose, when the rephotographing is not requested in the input,
    wherein the second dose is determined on the basis of at least one of a measured object thickness and object density.

12. The method of claim 11, wherein the determining of the existence/nonexistence of the density abnormality comprises acquiring the object density from the first image information and comparing the acquired object density with a predetermined reference value to determine the existence/nonexistence of the density abnormality.

13. A non-transitory computer-readable recording medium that stores a program that performs the method of claim 11 when executed by a computer.

\* \* \* \* \*